United States Patent [19]

Kitamura et al.

[11] Patent Number: 5,639,605
[45] Date of Patent: Jun. 17, 1997

[54] HUMAN INTERLEUKIN-3 RECEPTOR COMPONENT

[75] Inventors: Toshio Kitamura; Atsushi Miyajima, both of Palo Alto, Calif.

[73] Assignee: Schering Corporation, Kenilworth, N.J.

[21] Appl. No.: 161,988

[22] Filed: Dec. 3, 1993

Related U.S. Application Data

[63] Continuation of Ser. No. 688,355, Apr. 19, 1991, abandoned.
[51] Int. Cl.$^6$ .......................... C07K 14/705; C12N 5/10; C17N 15/12; G01N 33/53
[52] U.S. Cl. .................... 435/6; 435/7.1; 435/7.2; 435/69.1; 435/252.3; 435/320.1; 530/350; 536/23.5
[58] Field of Search ................. 435/69.1, 252.3, 435/320.1, 6, 7.1, 7.2; 536/23.5

[56] References Cited

PUBLICATIONS

Kaczmarski et al, Blood Rev 5(3) 1991, pp. 193–203.
Katamura et al, Blood 80(1) 1992, pp. 84–90.
Gearing et al, EMBO J. vol. 8, 1989, pp. 3667–3676.
Itoh et al, Science vol. 247, pp. 324–327, 1990.
Hyashida et al, PNAS 87, 1990, pp. 9655–9659.
Gorman et al PNAS 87, 1990, pp. 5459–5463.
Gesner et al, Blood 74(8) 1989, pp. 2652–2656.
Urdal et al, NY Acad. Science 554, 1989, pp. 167–176.
Reerk et al, Cell 50, 1987, p. 667.
Levin, Science 237, 1987.
Borgmann et al., Nature 319 1986, pp. 226–230 (sequence comparison only).
Yamamoto et al, Nature 319, 1986, pp. 230–234.
Nucleic Acids Res. 13:1505–13 (May 1985) Shimuzu et al. Nucleotide sequence of mouse IL–2 receptor cDNA and its comparison with the human IL–2 receptor sequence.
Cell 60: 941–51 (Mar. 23, 1990) Goodwin et al. Cloning of the Human and Murine Interleukin–7 Receptors: Demonstration of a Soluble Form and Homology . . .
P.N.A.S. 86:8946–50 (Nov. 1989) Sims et al. Cloning the interleukin1 receptor from human T cells.
Kitamura, et al. "Expression Cloning of the Human IL–3 Receptor cDNA Reveals a Shared Beta Subunit for the Human IL–3 and GM–CSF Receptors," Cell, 66(6): 1165–1174, Sep., 1991.
Kuwaki, et al. "Characterization of Human Interleukin–3 Receptors on a Multifactor–Dependent Cell Line," Biochemical and Biophysical Research Communications, 161(1):16–22, May, 1989.

Primary Examiner—John Ulm
Attorney, Agent, or Firm—Stephen C. Macevicz; Norman C. Dulak; Edwin P. Ching

[57] ABSTRACT

Nucleic acids encoding the α chain of the human interleukin-3 (IL-3) receptor, as well as the α chain itself, are provided. The α chain may be expressed with the β chain in cellular hosts to form compositions useful in screening agonists and antagonists of human IL-3.

19 Claims, 2 Drawing Sheets

HUMAN INTERLEUKIN-3 RECEPTOR COMPONENT

This application is a continuation of application U.S. Ser. No. 07/688,355, filed Apr. 19, 1991, now abandoned.

FIELD OF THE INVENTION

The invention relates generally to the human interleukin-3 (hIL-3) receptor, and more particularly, to the synthesis of a human IL-3 receptor component and to the use of the receptor component for screening agonists and antagonists of human IL-3.

BACKGROUND

Circulating blood cells are constantly replaced by newly developed cells. Replacement blood cells are formed in a process termed hematopoiesis which involves the production of at least eight mature blood cell types within two major lineages: (1) the myeloid lineage which includes red blood cells (erythrocytes), macrophages (monocytes), eosinophilic granulocytes, megakaryocytes (platelets), neutrophilic granulocytes, basophilic granulocytes (mast cells); and (2) the lymphoid lineage which includes T lymphocytes, and B lymphocytes, Burgess and Nicola, Growth Factors and Stem Cells (Academic Press, New York, 1983). Much of the control of blood cell formation is mediated by a group of interacting glycoproteins termed colony stimulating factors ($CSF_S$), including G-CSF, M-CSF, GM-CSF, and multi-CSF, or IL-3. These glycoproteins are so named because of the in vivo and in vitro assays used to detect their presence. Techniques for the clonal culture of hematopoietic cells in semisolid culture medium have been especially important in the development of in vitro assays. In such cultures, individual progenitor cells (i.e., cells developmentally committed to a particular lineage, but still capable of proliferation) are able to proliferate to form a colony of maturing progeny in a manner which is believed to be essentially identical to the comparable process in vivo. The role of $CSF_S$ in hematopoiesis is the subject of many reviews, and is of great interest to clinical investigators that must treat blood diseases or deficiencies, e.g. Metcalf, The Hemopoietic Colony Stimulating Factors (Elsevier, New York, 1984); Clark and Kamen, Science, Vol. 236, pgs. 1229–1237 (1987); Sachs, Science, Vol. 238, pgs. 1374–1379 (1987); Dexter et al, eds., Colony Stimulating Factors (Dekker, New York, 1990); and Morstyn et al, Cancer Investigation, Vol. 7, pgs. 443–456 (1989).

The biological effects of the $CSF_S$ are mediated by specific cell surface receptors, which may consist of one or more components. Recently, several of these have been cloned and characterized, e.g. Gearing et al, EMBO J., Vol. 8, pgs. 3667–3676 (1989)(low affinity α chain of human GM-CSF receptor); Itoh et al, Science, Vol. 247, pgs. 324–327 (1990)(low affinity mouse IL-3 receptor); and Hayashida et al, Proc. Natl. Acad. Sci., Vol. 87, pgs. 9655–9659 (1990)(β chain of human GM-CSF receptor). Besides contributing to an understanding of the signal transduction process, many of these receptors will be useful screening tools for agonists and antagonists of the natural ligand. In particular, such tools may lead to the development of non-protein agonists and antagonists which would obviate many of the difficulties associated with protein therapeutics, e.g. intravenous delivery, short serum half life, and the like.

SUMMARY OF THE INVENTION

The invention is directed to a component of the human IL-3 receptor, referred to herein as the α chain of the human IL-3 receptor, and to compositions thereof which bind with high affinity to human IL-3. Specifically such compositions include an α chain and β chain of the human IL-3 receptor that can operably associate to form a high affinity receptor for human IL-3. The invention includes allelic and genetically engineered variants of the α chain receptor, and nucleic acids encoding the α chain receptor and its allelic and genetically engineered variants. Preferably, the receptor component of the invention is selected from the group of polypeptides of the open reading frame defined by the amine acid sequence set forth in the Sequence Listing section. Although the listed sequence includes the intracellular domain of the α chain of the receptor, it is clear that truncated forms of the sequence which retain their extracellular and transmembrane domains and their ability of operably associate with the β chain fall within the concept of the invention.

The invention is based in part on the discovery that high affinity binding of human IL-3 involves the same β receptor component as high affinity binding of human GM-CSF. This lead to the discovery and cloning of a cDNA clone, designated pDUK-1, which expresses a protein that is capable of binding to human IL-3 with high affinity when operably associated with a human IL-3 (or equivalently a human GM-CSF) receptor β chain, such as encoded by the cDNA insert of pKH97 deposited with the American Type Culture Collection (ATCC) (Rockville, Md.) under accession number 40847. pDUK-1 has been deposited with the ATCC under accession number 75001. The invention includes nucleic acids (i) that are effectively homologous to the cDNA insert of pDUK-1, and (ii) that encode proteins that form high affinity IL-3 receptors in association with the β chain receptor protein, e.g. as encoded by pKH97. As used herein, high affinity in reference to IL-3 receptor binding means that IL-3 binds to the associated α and β chains of the receptor with a binding constant that is at least an order of magnitude less than that for binding to either component alone. More preferably, high affinity means that IL-3 binds to the associated α and β chains of the receptor with a binding constant. $K_d$, less than 1 nM; and most preferably, less than 200 pM.

DETAILED DESCRIPTION OF THE INVENTION

Figure 1:
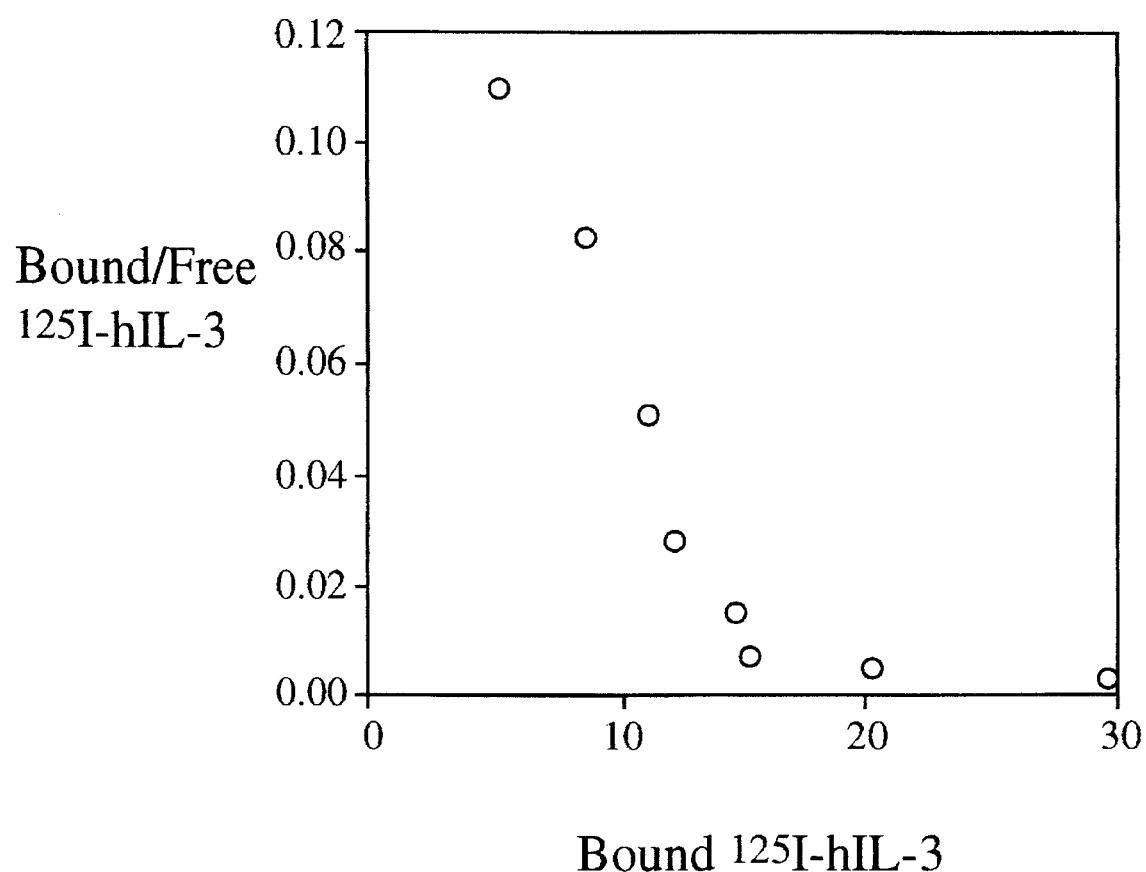
FIG. 1 illustrates the binding of $^{125}$I-labeled human IL-3 to COS 7 cells transiently co-transfected with KH97 and pDUK-1.

I. Obtaining and Expressing cDNAs for the Human IL-3 Receptor β Chain

The term "effectively homologous" as used herein means that the nucleotide sequence is capable of being detected by a hybridization probe derived from a cDNA clone of the invention. The exact numerical measure of hemology necessary to detect nucleic acids coding for a receptor α chain depends on several factors including (1) the hemology of the probe to non-α chain coding sequences associated with the target nucleic acids, (2) the stringency of the hybridization conditions, (3) whether single stranded or double stranded probes are employed, (4) whether RNA or DNA probes are employed, (5) the measures taken to reduce nonspecific binding of the probe, (6) the nature of the method used to label the probe, (7) the fraction of guanidine and cytosine bases in the probe, (8) the distribution of mismatches between probe and target, (9) the size of the probe, and the like. Preferably, an effectively homologous nucleic acid sequence is at least seventy percent (70%) homologous to the cDNA of the invention. More preferably, an effectively homologous nucleic acid is at least ninety percent (90%) homologous to the cDNA of the invention. Most particularly, an effectively homologous nucleic acid sequence is one whose cDNA can be isolated by a probe based on the nucleic acid sequence set forth in the Sequence Listing using a standard hybridization protocol with no more than a few false positive signals, e.g. less than a hundred. There is an extensive literature that provides guidance in selecting conditions for such hybridizations, e.g. Hames et al, Nucleic Acid Hybridization: A Practical Approach (IRL Press, Washington, D.C., 1985); Gray et al, Proc. Natl. Acad. Sci., Vol. 80, pgs. 5842–5846 (1983); Kafatos et al, Nucleic Acids Research, Vol. 7, pgs. 1541–1552 (1979); and Williams, Genetic Engineering, Vol. 1, pgs. 1–59 (1981), to name a few. By way of example, the nucleic acid of Sequence Listing can be used as a probe in colony hybridization assays as described by Benton and Davis, Science, Vol. 196, pg. 180 (1977). Preferably, low stringency conditions are employed for the probe employed (dissociation temperature depends on probe length). For example, for a probe of about 20–40 bases a typical prohybridization, hybridization, and wash protocol is as follows: (1) prohybridization: incubate nitrocellulose filters containing the denatured target DNA for 3–4 hours at 55° C. in 5× Denhardt's solution, 5× SSPE (20× SSPE consists of 174 g NaCl, 27,6 g $NaH_2PO_4-H_2O$, and 7.4 g EDTA in 800 ml $H_2O$ adjusted to pH 7.4 with 10N NaOH), 0.1% SDS, and 100 µg/ml denatured salmon sperm DNA, (2) hybridization: incubate filters in prehybridization solution plus probe at 55° C. for 2 hours, (3) wash: three 15 minute washes in 300–500 ml volumes of 6× SSC and 0.1% SDS at room temperature, followed by a final 1–1.5 minute wash in 300–500 ml of 1× SSC and 0.1% SDS at 55° C. Other equivalent procedures, e.g. employing organic solvents such as formamide, are well known in the art.

Hemology as the term is used herein is a measure of similarity between two nucleotide (or amine acid) sequences. Hemology is expressed as the fraction or percentage of matching bases (or amine acids) after two sequences (possibly of unequal length) have been aligned. The term alignment is used in the sense defined by Sankoff and Kruskal in chapter one of Time Warps, String Edits, and Macromolecules: The Theory and Practice of Sequence Comparison (Addison-Wesley, Reading, Mass., 1983). Roughly, two sequences are aligned by maximizing the number of matching bases (or amino acids) between the two sequences with the insertion of a minimal number of "blank" or "null" bases into either sequence to bring about the maximum overlap. Given two sequences, algorithms are available for computing their homology, e.g. Needleham and Wunsch, J. Mol. Biol., Vol. 48, pgs. 443–453 (1970); and Sankoff and Kruskal (cited above) pgs. 23–29. Also, commercial services and software packages are available for performing such comparisons, e.g. Intelligenetics, Inc. (Mountain View, Calif.); and University of Wisconsin Genetics Computer Group (Madison, Wis.).

Probes based on the nucleic acid sequence of the Sequence Listing can be synthesized on commercially available DNA synthesizers, e.g. Applied Biosystems model 381A, using standard techniques, e.g. Gait, Oligonucleotide Synthesis: A Practical Approach, (IRL Press, Washington D.C., 1984). It is preferable that the probe be at least 18–30 bases long. More preferably, the probe is at least 100–200 bases long. Probes of the invention can be labeled in a variety of ways standard in the art, e.g. radioactive labels, Berent et al, Biotechniques, pgs. 208–220 (May/June 1985), Meinkoth et al, Anal. Biochem., Vol. 138, pgs. 267–284 (1984), Szostak et al, Meth. Enzymol., Vol. 68, pgs. 419–429 (1979), and the like, and non-radioactive labels, Chu et al, DNA, Vol. 4, pgs. 327–331 (1985), Jablonski et al, Nucleic Acids Research, Vol. 14, pgs. 6115–6128 (1986), and the like.

Hybridization probes can also be used to screen candidate sources of α chain mRNA prior to library construction, e.g. by RNA blotting, Maniatis et al, Molecular Cloning: A Laboratory Manual, pgs. 202–203 (Cold Spring Harbor Laboratory, N.Y., 1982); or Hames and Higgins, eds., pgs. 139–143 in Nucleic Acids Hybridization (IRL Press, Washington, D.C., 1985). Sources of mRNA encoding the desired polypeptides include cell populations or cell lines that express, or can be induced to express, large numbers of IL-3 receptors on their surfaces, e.g. in excess of 3–5000.

Preferably, the α and β chains of the IL-3 receptor are co-transfected into a mammalian expression system (i.e. host-expression vector combination). Many reviews are available which provide guidance for making choices and/or modifications of specific mammalian expression systems, e.g. to name a few, Kucherlapati et al., Critical Reviews in Biochemistry, Vol. 16, Issue 4, pgs. 349–379 (1984), and Banerji et al., Genetic Engineering, Vol. 5, pgs. 19–31 (1983) review methods for transfecting and transforming mammalian cells; Reznikoff and Gold, eds., Maximizing Gone Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for linking and/or manipulating specific cDNAs and expression control sequences to create and/or modify expression vectors suitable for use with the present invention, e.g. Maniatis et al., Molecular Cloning: A Laboratory Manual (Cold Spring Harbor Laboratory, N.Y., 1982); Glover, DNA Cloning: A Practical Approach, Vol. I and II (IRL Press, Oxford, 1985), and Perbal, A Practical Guide to Molecular Cloning (John Wiley & Sons, N.Y., 1984), to name only a few.

Several DNA tumor viruses have been used as vectors for mammalian hosts. Particularly important are the numerous vectors which comprise SV40 replication, transcription, and/or translation control sequences coupled to bacterial replication control sequences, e.g. the pcD vectors developed by Okayama and Berg, disclosed in Mol. Cell. Biol., Vol. 2, pgs. 161–170 (1982) and Mol. Cell. Biol., Vol. 3, pgs. 280–289 (1983), both of which are incorporated herein by reference; the SV40 vectors disclosed by Hamer in Genetic Engineering, Vol. 2, pgs. 83–100 (1980), and U.S. Pat. No. 4,599,308, both of which are incorporated herein by reference; and the vectors additionally containing adenovirus regulatory elements, disclosed by Kaufman and Sharp, in Mol. Cell. Biol., Vol. 2, pgs. 1304–1319 (1982), and Clark et at., in U.S. Pat. No. 4,675,285, both of which are incorporated herein by reference. COS7 monkey cells, described by Gluzman, Cell, Vol. 23, pgs. 175–182 (1981) and available from the ATCC (accession no. CRL 1651), are usually the preferred hosts for the above vectors. SV40-based vectors suitable for mammalian receptor expression have been developed by Aruffo and Seed, Proc. Natl. Acad. Sci., Vol. 84, pgs. 3365–3369 and 8573–8577 (1987).

II. Binding Assays

Binding assays are accomplished by letting a ligand of unknown specificity or affinity compete with a known amount or concentration of labeled human IL-3 for receptor binding sites of a sample of cells transfected or transformed with pDUK-1, or its equivalent. Preferably, the IL-3 is labeled by radioiodination using standard protocols, e.g. reaction with 1,3,4,6-tetrachloro-3α,6α-diphenylglycouril described by Fraker et al, Biochem Biophys. Res. Commun., Vol. 80, pgs. 849–857 (1978)(and available from Pierce Chemical Co. as Iodogen). Generally, the binding assay is conducted as described by Lowenthal et al, J. Immunol., Vol 140, pgs. 456–464 (1988), which is incorporated by reference. Briefly, aliquots of cells are incubated in the presence of $^{125}$I-labeled human IL-3 in a final volume of 200 μl culture medium in microfuge tubes at 4° C. Cell-bound $^{125}$I-labeled IL-3 was separated from non-bound $^{125}$I-labeled IL-3 by centrifugation through an oil gradient (10, 000×G for 2 min). Nonspecific binding is measured in the presence of a 100-fold excess of partially purified unlabeled human IL-3.

EXAMPLES

Example I. Construction of cDNA Library from TF-1 Cells and Isolation of pDUK-1

Figure 2:
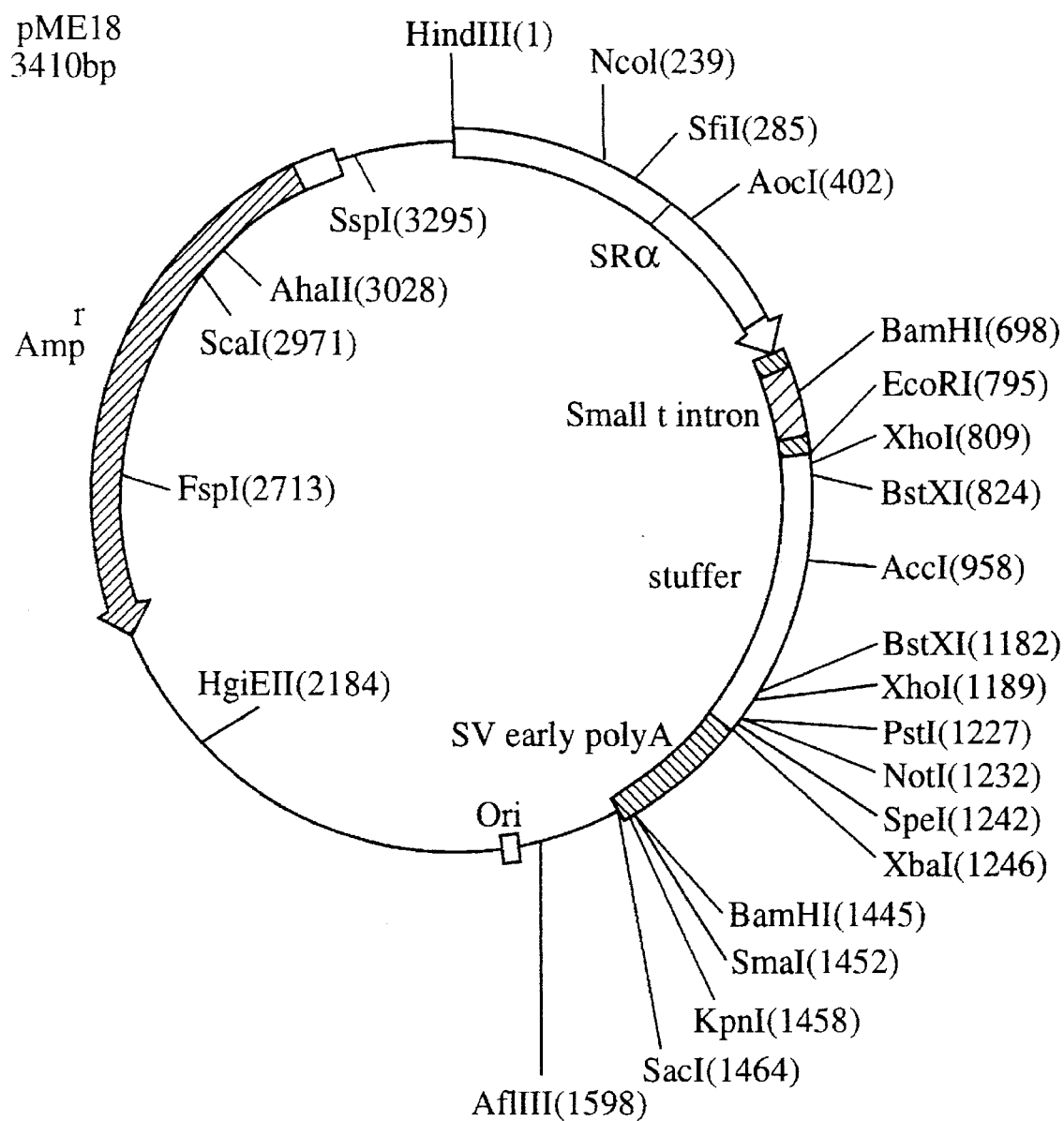
FIG. 2 is a restriction map of the vector pME18.

Poly(A)$^+$ RNA from TF-1 cells (Kitamura et al, J. Cell. Physiol., Vol. 140, pgs. 323–334 (1989)) cultured in the presence of hIL-3 (5 ng/ml) was isolated by the guanidium isothianate method (Chirgwin et al, Biochemistry, Vol. 18, pgs. 5294–5299 (1978)), and was converted to double-stranded cDNA using oligo(dT) primers. After Bst XI linkers (containing Xba I sites) were ligated to both ends of the cDNAs, the cDNAs were size-fractionated through an agarose gel. cDNAs greater than 1.0 kb were digested with Xba I and ligated with Xba I-digested pME18, an SV40-based mammalian expression vector, diagrammed in FIG. 2, to form a library of about 3×10$^6$ independent clones. About 3 μg of miniprep DNA from pools of 3×10$^3$ clones was co-transfected with 50 ng of pKH97 (carrying a cDNA insert encoding the β chain of the hGM-CSF receptor) into COS 7 cells by electroporation (0.4 gap cuvette at 300 volts and 300 μF using a Gene Pulser (BioRad, Richmond, Calif.)). The Cos 7 cells were incubated for 72 hours prior to screening. pDUK-1 was isolated by screening for cells capable of high affinity binding to $^{125}$I-labelled hIL-3. 10 nM $^{125}$I-labelled hIL-3 was added to transfected Cos 7 cells in a Chamber Slide (Labo-Tek), after which cells binding $^{125}$I-labelled hIL-3 were identified by microscopic autoradiography.

Example II. Binding of hIL-3 to COS 7 Cells Co-transfected with pKH97 and pDUK-1

A total of 5 μg of equal amounts of pKH97 and pDUK-1 plasmid DNA was transfected into semi-confluent COS 7 cells by the DEAE-dextran method. 72 hours after transfection, the cells were harvested and analyzed in IL-3 binding assays. Duplicates of 2×10$^5$ COS 7 cells in 0.1 ml of RPMI 1640 containing 10% fetal calf serum, 2 mM EDTA, 0.02% sodium azide and 20 mM Hepes (pH 7.4) were incubated for 3 h at 4° C. with various concentrations of $^{125}$I-labeled human IL-3 with or without an excess amount of non-labeled human IL-3. The cell-bound radioactivity was measured by separating the cells from free ligand by centrifugation through an oil layer, as described by Schreurs et al, Growth Factors, Vol. 2, pgs. 221–233 (1990). IL-3 was iodinated by a standard protocol, Chiba et al, Leukemia, Vol. 4, pgs. 22–36 (1990). Briefly, 5 μg of E. coli-produced human IL-3 was incubated in 30–50 μl of 50 mM sodium borate buffer (pH 8.0) with 1 mCi of the dried Bolton and Hunter reagent for 12–16 h at 4° C. Glycine was added to 2.5 mg/ml to stop the reaction and the iodinated IL-3 was separated from the free Bolton and Hunter reagent by a PD-10 column. The iodinated human IL-3 had a specific radioactivity of 4–8×10$^7$ cpm/μg and was stable for about two months in Hepes-buffered Hank's balanced salt solution containing 0.1% gelatin, 0.1% bovine serum albumin, and 0.02% sodium azide.

FIG. 1 shows the receptor binding data. Open circles correspond to COS 7 cells transfected with pKH125 and pKH97. Scatchard analysis (via the LIGAND program, De Lean et al, Mol. Pharmacol., Vol. 21, pgs. 5–16 (1982)) of the binding data indicated an equilibrium binding constant, $K_d$, of 100 pM.

Example III. Co-transfection of pKH97 and pDUK-1 into NIH3T3 Cells

A DNA fragment containing the neomycin-resistance gene, neo, was inserted into pKH97 downstream of the SRα promoter to form pKH97neo, and a DNA fragment containing the hygromycin-resistance gene, hyg, was inserted into pDUK-1 downstream of the SRα promoter to form pDUK-1hyg. NIH3T3 cells were stably transfected with pKH97neo and pDUK-1hyg by the calcium-phosphate procedure, described by Chen and Okayama, Mol. Cell. Biol., Vol. 7, pgs. 2745–2752 (1987), which reference is incorporated by reference. Stable co-transfectants were selected by 1 mg/ml of G418 and 1 mg/ml hygromycin. Analysis of the binding of $^{125}$I-labelled hIL-3 indicated a $K_d$ of about 100 pM.

Example IV. Use of Stably Co-transfected NIH3T3 Cells to Screen for IL-3 Antagonists Aliquots of NIH3T3 cells co-transfected with pKH97neo and pDUK-1hyg as described above are distributed to wells of microtiter plates in 200 μl of medium containing $^{125}$I-labeled human IL-3 at concentrations of 100 pM, 500 pM, and 1 nM. 100 μl samples of microbial supernatants free of cells are added to the transfected NIH3T3 cells at each of the different concentrations of $^{125}$I-labeled IL-3. After incubating for 3 hours the NIH3T3 cells are harvested and assayed for bound radioactivity. NIH3T3 cells with low counts of bound radioactivity correspond microbial samples containing candidate antagonists or agonists of human IL-3.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited pKH97 and pDUK-1 with the. American Type Culture Collection, Rockville, Md., USA (ATCC), under accession numbers 40847 and 75001, respectively. These deposits were made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited plasmids is not to be construed as a license to practice the invention in contravention of the rights granted under the authority of any government in accordance with its patent laws.

We claim:

1. A recombinant or isolated nucleic acid comprising sequence encoding human interleukin-3 receptor subunit α-chain.

2. The nucleic acid of claim 1 wherein said α-chain comprises mature SEQ ID NO 2.

3. The nucleic acid of claim 1, which further comprises a sequence which encodes an interleukin-3 receptor subunit β-chain.

4. The nucleic acid of claim 3 wherein the expression products of said sequences can combine to form a high affinity interleukin-3 receptor exhibiting a binding constant ($K_d$) with human interleukin-3 of less than 1 nM.

5. The nucleic acid of claim 1, further comprising an SV40 replication, transcription, and/or control sequence.

6. A cell comprising a nucleic acid of claim 1.

7. The cell of claim 6, further comprising interleukin-3 receptor β subunit or nucleic acid encoding interleukin-3 receptor β subunit.

8. A recombinant or isolated nucleic acid encoding a polypeptide comprising mature SEQ ID NO 2.

9. A cell comprising a nucleic acid of claim 8.

10. The cell of claim 1, further comprising interleukin-3 receptor β subunit or a nucleic acid encoding interleukin-3 receptor β subunit.

11. The nucleic acid of claim 8, comprising a mature subunit encoding portion of SEQ ID NO 1.

12. A polypeptide comprising the extracellular and transmembrane domains of human interleukin-3 receptor α subunit and lacking a complete natural intracellular domain, wherein said polypeptide can combine with interleukin-3 receptor β subunit to form a high affinity receptor which can bind human interleukin-3.

13. The polypeptide of claim 12, wherein said high affinity receptor will bind human interleukin-3 with a Kd of less than 1 nM.

14. A nucleic acid encoding said polypeptide of claim 12.

15. A method of identifying an interleukin-3 receptor ligand comprising:

a) contacting a high affinity receptor of claim 12 with a candidate ligand; and b) measuring the binding of said receptor to interleukin-3; whereby said ligand is identified by measurement of binding of said interleukin-3 to said receptor.

16. The method of claim 15, wherein said polypeptide lacks any of the intracellular domain of said subunit.

17. The method of claim 15, wherein said candidate ligand is a sequence variant of IL-3.

18. The method of claim 15, wherein said IL-3 is labeled.

19. The method of claim 15, wherein said high affinity receptor is formed on a cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1460 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 147..1280

( x i ) SEQUENCE DESCRIPTION: SEQ ID NO:1:

```
GCACACGGGA AGATATCAGA AACATCCTAG GATCAGGACA CCCCAGATCT TCTCAACTGG      60

AACCACGAAG GCTGTTTCTT CCACACAGCA CTTTGATCTC CATTTAAGCA GGCACCTCTG     120

TCCTGCGTTC CGGAGCTGCG TTCCCG ATG GTC CTC CTT TGG CTC ACG CTG CTC     173
                             Met Val Leu Leu Trp Leu Thr Leu Leu
                              1               5

CTG ATC GCC CTG CCC TGT CTC CTG CAA ACG AAG GAA GAT CCA AAC CCA     221
Leu Ile Ala Leu Pro Cys Leu Leu Gln Thr Lys Glu Asp Pro Asn Pro
 10              15                  20                  25

CCA ATC ACG AAC CTA AGG ATG AAA GCA AAG GCT CAG CAG TTG ACC TGG     269
Pro Ile Thr Asn Leu Arg Met Lys Ala Lys Ala Gln Gln Leu Thr Trp
             30                  35                  40

GAC CTT AAC AGA AAT GTG ACC GAT ATC GAG TGT GTT AAA GAT GCC GAC     317
Asp Leu Asn Arg Asn Val Thr Asp Ile Glu Cys Val Lys Asp Ala Asp
         45                  50                  55

TAT TCT ATG CCG GCA GTG AAC AAT AGC TAT TGC CAG TTT GGA GCA ATT     365
Tyr Ser Met Pro Ala Val Asn Asn Ser Tyr Cys Gln Phe Gly Ala Ile
     60                  65                  70

TCC TTA TGT GAA GTG ACC AAC TAC ACC GTC CGA GTG GCC AAC CCA CCA     413
Ser Leu Cys Glu Val Thr Asn Tyr Thr Val Arg Val Ala Asn Pro Pro
 75                  80                  85

TTC TCC ACG TGG ATC CTC TTC CCT GAG AAC AGT GGG AAG CCT TGG GCA     461
Phe Ser Thr Trp Ile Leu Phe Pro Glu Asn Ser Gly Lys Pro Trp Ala
 90                  95                 100                 105

GGT GCG GAG AAT CTG ACC TGC TGG ATT CAT GAC GTG GAT TTC TTG AGC     509
Gly Ala Glu Asn Leu Thr Cys Trp Ile His Asp Val Asp Phe Leu Ser
                 110                 115                 120

TGC AGC TGG GCG GTA GGC CCG GGG GCC CCC GCG GAC GTC CAG TAC GAC     557
Cys Ser Trp Ala Val Gly Pro Gly Ala Pro Ala Asp Val Gln Tyr Asp
             125                 130                 135

CTG TAC TTG AAC GTT GCC AAC AGG CGT CAA CAG TAC GAG TGT CTT CAC     605
Leu Tyr Leu Asn Val Ala Asn Arg Arg Gln Gln Tyr Glu Cys Leu His
         140                 145                 150

TAC AAA ACG GAT GCT CAG GGA ACA CGT ATC GGG TGT CGT TTC GAT GAC     653
Tyr Lys Thr Asp Ala Gln Gly Thr Arg Ile Gly Cys Arg Phe Asp Asp
     155                 160                 165

ATC TCT CGA CTC TCC AGC GGT TCT CAA AGT TCC CAC ATC CTG GTG CGG     701
Ile Ser Arg Leu Ser Ser Gly Ser Gln Ser Ser His Ile Leu Val Arg
 170                 175                 180                 185

GGC AGG AGC GCA GCC TTC GGT ATC CCC TGC ACA GAT AAG TTT GTC GTC     749
Gly Arg Ser Ala Ala Phe Gly Ile Pro Cys Thr Asp Lys Phe Val Val
                 190                 195                 200
```

-continued

| | | | | | | | | | | | | | | | | |
|---|---|---|---|---|---|---|---|---|---|---|---|---|---|---|---|---|
| TTT | TCA | CAG | ATT | GAG | ATA | TTA | ACT | CCA | CCC | AAC | ATG | ACT | GCA | AAG | TGT | 797 |
| Phe | Ser | Gln | Ile | Glu | Ile | Leu | Thr | Pro | Pro | Asn | Met | Thr | Ala | Lys | Cys | |
| | | | 205 | | | | 210 | | | | | | 215 | | | |
| AAT | AAG | ACA | CAT | TCC | TTT | ATG | CAC | TGG | AAA | ATG | AGA | AGT | CAT | TTC | AAT | 845 |
| Asn | Lys | Thr | His | Ser | Phe | Met | His | Trp | Lys | Met | Arg | Ser | His | Phe | Asn | |
| | | 220 | | | | | 225 | | | | | 230 | | | | |
| CGC | AAA | TTT | CGC | TAT | GAG | CTT | CAG | ATA | CAA | AAG | AGA | ATG | CAG | CCT | GTA | 893 |
| Arg | Lys | Phe | Arg | Tyr | Glu | Leu | Gln | Ile | Gln | Lys | Arg | Met | Gln | Pro | Val | |
| | 235 | | | | | 240 | | | | | 245 | | | | | |
| ATC | ACA | GAA | CAG | GTC | AGA | GAC | AGA | ACC | TCC | TTC | CAG | CTA | CTC | AAT | CCT | 941 |
| Ile | Thr | Glu | Gln | Val | Arg | Asp | Arg | Thr | Ser | Phe | Gln | Leu | Leu | Asn | Pro | |
| 250 | | | | | 255 | | | | | 260 | | | | | 265 | |
| GGA | ACG | TAC | ACA | GTA | CAA | ATA | AGA | GCC | CGG | GAA | AGA | GTG | TAT | GAA | TTC | 989 |
| Gly | Thr | Tyr | Thr | Val | Gln | Ile | Arg | Ala | Arg | Glu | Arg | Val | Tyr | Glu | Phe | |
| | | | 270 | | | | | 275 | | | | | 280 | | | |
| TTG | AGC | GCC | TGG | AGC | ACC | CCC | CAG | CGC | TTC | GAG | TGC | GAC | CAG | GAG | GAG | 1037 |
| Leu | Ser | Ala | Trp | Ser | Thr | Pro | Gln | Arg | Phe | Glu | Cys | Asp | Gln | Glu | Glu | |
| | | | | 285 | | | | 290 | | | | | 295 | | | |
| GGC | GCA | AAC | ACA | CGT | GCC | TGG | CGG | ACG | TCG | CTG | CTG | ATC | GCG | CTG | GGG | 1085 |
| Gly | Ala | Asn | Thr | Arg | Ala | Trp | Arg | Thr | Ser | Leu | Leu | Ile | Ala | Leu | Gly | |
| | | 300 | | | | | 305 | | | | | 310 | | | | |
| ACG | CTG | CTG | GCC | CTG | GTC | TGT | GTC | TTC | GTG | ATC | TGC | AGA | AGG | TAT | CTG | 1133 |
| Thr | Leu | Leu | Ala | Leu | Val | Cys | Val | Phe | Val | Ile | Cys | Arg | Arg | Tyr | Leu | |
| | 315 | | | | | 320 | | | | | 325 | | | | | |
| GTG | ATG | CAG | AGA | CTC | TTT | CCC | CGC | ATC | CCT | CAC | ATG | AAA | GAC | CCC | ATC | 1181 |
| Val | Met | Gln | Arg | Leu | Phe | Pro | Arg | Ile | Pro | His | Met | Lys | Asp | Pro | Ile | |
| 330 | | | | | 335 | | | | | 340 | | | | | 345 | |
| GGT | GAC | AGC | TTC | CAA | AAC | GAC | AAG | CTG | GTG | GTC | TGG | GAG | GCG | GGC | AAA | 1229 |
| Gly | Asp | Ser | Phe | Gln | Asn | Asp | Lys | Leu | Val | Val | Trp | Glu | Ala | Gly | Lys | |
| | | | | 350 | | | | | 355 | | | | | 360 | | |
| GCC | GGC | CTG | GAG | GAG | TGT | CTG | GTG | ACT | GAA | GTA | CAG | GTC | GTG | CAG | AAA | 1277 |
| Ala | Gly | Leu | Glu | Glu | Cys | Leu | Val | Thr | Glu | Val | Gln | Val | Val | Gln | Lys | |
| | | | 365 | | | | | 370 | | | | | 375 | | | |
| ACT | TGAGACTGGG | GTTCAGGGCT | TGTGGGGGTC | TGCCTCAATC | TCCCTGGCCG | | | | | | | | | | | 1330 |
| Thr | | | | | | | | | | | | | | | | |

GGCCAGGCGC CTGCACAGAC TGGCTGCTGG ACCTGCGCAC GCAGCCCAGG AATGGACATT    1390

CCTAACGGGT GGCCTGTGTA ATTTCGTTGG GCATGGGAGA TGCCGAAGCT GCCAGGAAGA    1450

AGAACAGAAC    1460

( 2 ) INFORMATION FOR SEQ ID NO:2:

( i ) SEQUENCE CHARACTERISTICS:
        ( A ) LENGTH: 378 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Val | Leu | Leu | Trp | Leu | Thr | Leu | Leu | Ile | Ala | Leu | Pro | Cys | Leu |
|---|---|---|---|---|---|---|---|---|---|---|---|---|---|---|
| 1 | | | | 5 | | | | | 10 | | | | | 15 |

| Leu | Gln | Thr | Lys | Glu | Asp | Pro | Asn | Pro | Ile | Thr | Asn | Leu | Arg | Met |
|---|---|---|---|---|---|---|---|---|---|---|---|---|---|---|
| | | | 20 | | | | | 25 | | | | | 30 | |

| Lys | Ala | Lys | Ala | Gln | Gln | Leu | Thr | Trp | Asp | Leu | Asn | Arg | Asn | Val | Thr |
|---|---|---|---|---|---|---|---|---|---|---|---|---|---|---|---|
| | | | 35 | | | | 40 | | | | | 45 | | | |

| Asp | Ile | Glu | Cys | Val | Lys | Asp | Ala | Asp | Tyr | Ser | Met | Pro | Ala | Val | Asn |
|---|---|---|---|---|---|---|---|---|---|---|---|---|---|---|---|
| | | 50 | | | | | 55 | | | | | 60 | | | |

| Asn | Ser | Tyr | Cys | Gln | Phe | Gly | Ala | Ile | Ser | Leu | Cys | Glu | Val | Thr | Asn |
|---|---|---|---|---|---|---|---|---|---|---|---|---|---|---|---|
| 65 | | | | | 70 | | | | | 75 | | | | | 80 |

```
Tyr Thr Val Arg Val Ala Asn Pro Pro Phe Ser Thr Trp Ile Leu Phe
            85                  90                     95

Pro Glu Asn Ser Gly Lys Pro Trp Ala Gly Ala Glu Asn Leu Thr Cys
            100             105                 110

Trp Ile His Asp Val Asp Phe Leu Ser Cys Ser Trp Ala Val Gly Pro
        115             120                 125

Gly Ala Pro Ala Asp Val Gln Tyr Asp Leu Tyr Leu Asn Val Ala Asn
        130             135             140

Arg Arg Gln Gln Tyr Glu Cys Leu His Tyr Lys Thr Asp Ala Gln Gly
145                 150             155                     160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180             185                 190

Ile Pro Cys Thr Asp Lys Phe Val Val Phe Ser Gln Ile Glu Ile Leu
        195             200                 205

Thr Pro Pro Asn Met Thr Ala Lys Cys Asn Lys Thr His Ser Phe Met
    210             215             220

His Trp Lys Met Arg Ser His Phe Asn Arg Lys Phe Arg Tyr Glu Leu
225                 230             235                     240

Gln Ile Gln Lys Arg Met Gln Pro Val Ile Thr Glu Gln Val Arg Asp
                245             250             255

Arg Thr Ser Phe Gln Leu Leu Asn Pro Gly Thr Tyr Thr Val Gln Ile
            260             265             270

Arg Ala Arg Glu Arg Val Tyr Glu Phe Leu Ser Ala Trp Ser Thr Pro
        275             280             285

Gln Arg Phe Glu Cys Asp Gln Glu Glu Gly Ala Asn Thr Arg Ala Trp
    290             295             300

Arg Thr Ser Leu Leu Ile Ala Leu Gly Thr Leu Leu Ala Leu Val Cys
305             310             315                     320

Val Phe Val Ile Cys Arg Arg Tyr Leu Val Met Gln Arg Leu Phe Pro
            325             330             335

Arg Ile Pro His Met Lys Asp Pro Ile Gly Asp Ser Phe Gln Asn Asp
        340             345             350

Lys Leu Val Val Trp Glu Ala Gly Lys Ala Gly Leu Glu Glu Cys Leu
        355             360             365

Val Thr Glu Val Gln Val Val Gln Lys Thr
    370             375
```